(12) United States Patent
Abbott

(10) Patent No.: US 10,369,294 B2
(45) Date of Patent: Aug. 6, 2019

(54) FLUID DOSE DISPENSING APPARATUS

(71) Applicant: Kevin Abbott, Hertfordshire (GB)

(72) Inventor: Kevin Abbott, Hertfordshire (GB)

( * ) Notice: Subject to any disclaimer, the term of this patent is extended or adjusted under 35 U.S.C. 154(b) by 0 days.

(21) Appl. No.: 15/293,317

(22) Filed: Oct. 14, 2016

(65) Prior Publication Data
US 2017/0030592 A1    Feb. 2, 2017

Related U.S. Application Data

(60) Division of application No. 13/746,493, filed on Jan. 22, 2013, and a continuation-in-part of application No. PCT/GB2011/001111, filed on Jul. 22, 2011.

(51) Int. Cl.
| | | |
|---|---|---|
| *A61M 5/315* | (2006.01) | |
| *F04B 39/00* | (2006.01) | |
| *F24D 19/00* | (2006.01) | |
| *B67D 7/74* | (2010.01) | |

(52) U.S. Cl.
CPC ..... *A61M 5/31596* (2013.01); *F04B 39/0016* (2013.01); *F24D 19/0092* (2013.01); *B67D 7/74* (2013.01)

(58) Field of Classification Search
CPC ... F04B 39/0016; B65D 25/08; B65D 25/082; B65D 25/085; B65D 2081/001; B65D 81/32; B65D 81/325; B65D 81/3255; B65D 2217/00; B05B 11/02; A61M 5/3159; A61M 5/31591; A61M 5/31593; A61M 5/31595; A61M 5/31565; A61M 5/31511; A61M 2005/287; A61M 5/31596
USPC ............................. 92/181 R, 181 P; 604/231
See application file for complete search history.

(56) References Cited

U.S. PATENT DOCUMENTS

| | | | | |
|---|---|---|---|---|
| 464,223 | A * | 12/1891 | Fasoldt ............... | F04B 39/0016 417/259 |
| 1,615,380 | A * | 1/1927 | Hill ........................ | F04B 9/14 222/383.1 |
| 2,610,628 | A * | 9/1952 | Lockhart .............. | B01L 3/5082 206/221 |
| 2,709,433 | A * | 5/1955 | Sorenson .......... | A61M 5/31551 604/236 |
| 3,326,215 | A * | 6/1967 | Sarnoff ................. | A61M 5/284 604/90 |
| 3,437,242 | A * | 4/1969 | Poitras ............... | B65D 81/3255 222/129 |

(Continued)

FOREIGN PATENT DOCUMENTS

KR    1020170122938 A  * 11/2017  ............. B65D 81/32

*Primary Examiner* — Patrick M. Buechner
(74) *Attorney, Agent, or Firm* — Invention To Patent Service; Alex Hobson

(57) ABSTRACT

Apparatus for dispensing a dose of fluid, the apparatus comprising a dispensing vessel with a dispensing outlet, the vessel having a piston and a vessel wall defining a cylinder in which the piston may move under pressure from a first position to a second position, wherein the apparatus has a bypass passage that extends through the first piston and has a valve member that is opened by a valve actuating plunger in the piston that moves within the piston to push the valve open when the valve actuating plunger abuts a shoulder at or near the second position in the vessel; wherein the shoulder at the second position is an annular shoulder and the apparatus is adapted to dispense fluid in a sequence of stages comprising a mixing stage and a dispensing stage.

9 Claims, 7 Drawing Sheets

(56) References Cited

U.S. PATENT DOCUMENTS

| | | | | |
|---|---|---|---|---|
| 3,489,147 | A * | 1/1970 | Shaw | A61J 1/2093 222/137 |
| 3,756,390 | A * | 9/1973 | Abbey | A61M 5/284 206/219 |
| 3,766,917 | A * | 10/1973 | Wimmer | A61M 5/31596 222/136 |
| 4,615,341 | A * | 10/1986 | Marzolf | A61B 5/15003 600/578 |
| 5,080,649 | A * | 1/1992 | Vetter | A61M 5/31596 604/191 |
| 5,298,024 | A * | 3/1994 | Richmond | A61M 5/31595 604/191 |
| 5,935,101 | A * | 8/1999 | Kato | A61M 5/284 604/181 |
| 6,149,628 | A * | 11/2000 | Szapiro | A61M 5/31596 604/191 |
| 2005/0245880 | A1* | 11/2005 | Howlett | A61M 5/284 604/231 |
| 2006/0142701 | A1* | 6/2006 | Thorne, Jr. | A61M 5/31596 604/218 |
| 2009/0062740 | A1* | 3/2009 | Thorne, Jr. | A61M 5/284 604/191 |
| 2009/0088724 | A1* | 4/2009 | Chebator | A61M 5/1454 604/508 |
| 2012/0265171 | A1* | 10/2012 | Thorne, Jr. | A61M 5/31596 604/518 |
| 2012/0323173 | A1* | 12/2012 | Thorne, Jr. | A61M 5/31596 604/89 |
| 2014/0060664 | A1* | 3/2014 | Abbott | F04B 9/14 137/101.11 |
| 2015/0217924 | A1* | 8/2015 | Cho | B65D 51/2892 206/219 |

\* cited by examiner

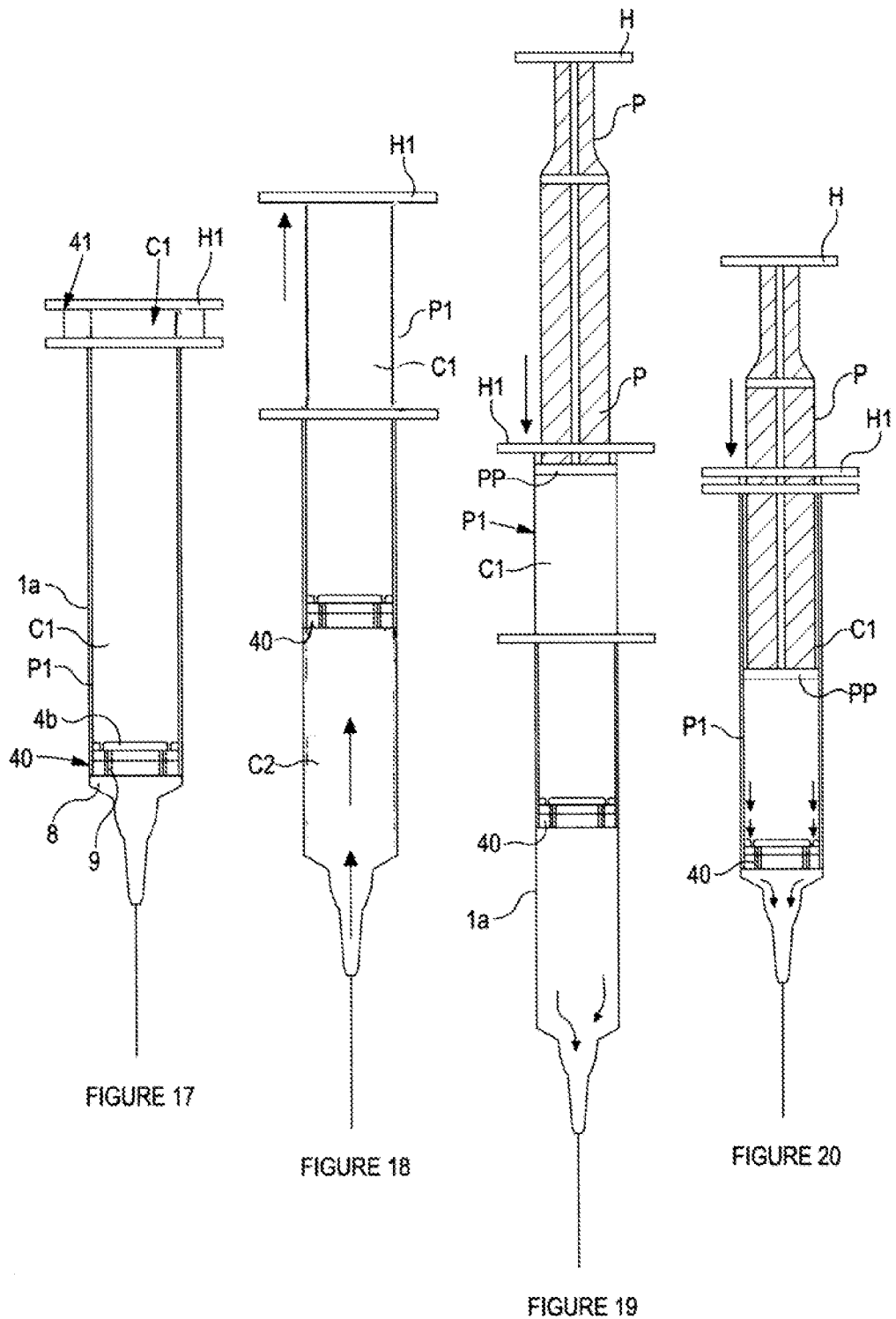

FLUID DOSE DISPENSING APPARATUS

CROSS-REFERENCE TO RELATED APPLICATIONS

This application is a divisional application of U.S. patent application No. 13/746,493, filed on Jan. 22, 2013 and currently pending, which is a continuation if part of International Application PCT/GB2011/001111, with an international filing date of Jul. 22, 2011 and entitled Fluid Dose Dispensing Apparatus.

FIELD OF THE INVENTION

The present invention concerns improvements in and relating to apparatus for dispensing doses of fluids. In one aspect it concerns apparatus for dosing a fluid-filled, eg water-filled, system with a dose of one or more chemicals/treatment fluid. The invention may have applicability to treating central heating systems with rust inhibitor liquids or applicability to a wide range of other uses including but not limited to treating fluid-filled systems as diverse as scientific or industrial laboratory flow systems, medical systems such as drips/circulatory feeds for patients or automotive/transport or other industrial flow systems wherever there is a need for dosing the fluid in the system with treatment fluids/chemicals (is fluid of a type or content different from the fluid normally flowing in the system) from time-to-time, in another aspect the invention provides piston-operated devices such as syringes or piston-operated cartridges for dispensing doses of fluids as diverse as two-part adhesives or multiple shots of drinks.

BACKGROUND TO THE INVENTION

Modern central heating systems, and especially pressurised/sealed central heating systems, require treatment with anti-freeze, rust inhibitor chemicals and/or descaling or limescale inhibiting chemicals or other chemicals on a regular basis to ensure good maintenance of the system. In general this is done by service engineers/plumbers who carry out regular site visits to premises with such systems. The specialized nature of the task when dealing with pressurised/sealed central heating systems has lead to development of specialized apparatus and procedures for the purpose and there are a number of relevant patents.

Addition of rust inhibitor chemicals to non-pressurised systems is the subject of patent applications and patents from twenty years ago and earlier, as exemplified by UK patent GB 2162164B and its citations. GB 2162164B concerns use of a sealed vessel to receive the rust inhibitor. A volume of water is added into the vessel as diluent/flushing medium. The vessel has an inlet for pressurised air from a separate pump such as a bicycle pump to drive the chemical-laden fluid into a radiator of the non-pressurised central heating system via a bleed valve of the radiator. This approach introduces air into the system but this is not a major problem for the non-pressurised system since the air can simply be bled back out subsequently. The process is relatively risk-free and can be carried out by a home-owner. It does not need to be done by a professional.

When dealing with a pressurised central heating system the process is made substantially more difficult by the very fact of pressurization. Some have sought to address the problem by introducing the dosing vessel into the circuit of the pressurised central heating system between the cold water supply pipe and central heating return pipe of the system so that the inflowing cold water swirls in the vessel and carries the chemical up from the floor of the vessel into the central heating system. An example of this is disclosed in UK patent application G62442008A where a pair of hoses is provided one to couple the vessel to the cold water supply pipe and the other to couple the vessel to the central heating return pipe.

The arrangement in GE42442008A enables dosing to be carried out relatively safely since the hoses are coupled in place and valves to the hoses are only opened when the circuit through the vessel is water-tight. However, the delivery of the water and chemicals is inefficient and relies on a sufficient flow of water to have passed through the vessel to transfer substantially the whole dose of chemical into the system before the vessel and hoses can be uncoupled from the system. This may entail twenty or more liters of water having to pass through a liter-sized vessel before the plumber/service-engineer can be reasonably sure that all of the chemical has been substantially fully passed/flushed into the system. For a plumber/service-engineer on the clock this can be a significant waste of his time (and the client's money). Furthermore, this can be wasteful of water and incur extra water meterage charges for the customer.

It is a first object of the present invention to provide an improved method and apparatus for dosing a fluid/water system such as, for example, a central heating system, or a medical drip or any other flow system with one or more chemicals/treatment fluid and which allows rapid and substantially accurate dosing with minimal usage of water/fluid to flush the chemicals/treatment fluid into the system.

A further set of problems arise with regard to piston-operated devices for dispensing fluids, and especially dosing or administering two or more doses of the same or different materials at least one of which is fluid (the materials may both be fluid or be one liquid and the other a solid soluble or transportable in the fluid) materials which should be unmixed/kept apart prior to or during delivery. Such devices may include syringes for delivery of multiple medicaments or even for drinks that are to be dispensed in shots, and cartridges for mastic guns or other plunger devices. Existing syringes that deliver multiple materials generally do so in parallel or provide little control over mixing of the materials and generally fail to provide an effective way of dispensing two materials sequentially with a single plunger or in a staged controlled manner.

It is thus a further object of the present invention to address these latter problems and provide improved piston-operated devices such as syringes or cartridges for mastic guns or other plunger devices that allow two or more materials to be delivered sequentially or in a staged manner.

SUMMARY OF THE INVENTION

According to one aspect of the present invention there is provided apparatus for dispensing a dose of fluid, the apparatus comprising a dispensing vessel with a dispensing outlet, the vessel having a piston and the vessel wall defining a cylinder in which the piston may move under pressure from a first position to a second position, wherein the apparatus has a bypass passage that extends through the first piston and has a valve member that is opened by a valve actuating plunger in the piston that moves within the piston to push the valve open when the valve actuating plunger abuts a shoulder at or near the second position in the vessel.

Preferably the apparatus is adapted to dispense two or more doses of fluid in sequence and the vessel has at least a first chamber and a second chamber separated by the piston. Suitably the first chamber is proximate a dispensing outlet end of the vessel and the second chamber is remote from the dispensing outlet end and the first position of the piston corresponds to a position at which the first chamber of the vessel contains a first dose of fluid to be dispensed and the second position corresponds to substantially complete emptying of the first chamber of the vessel, whereupon the opening of the valve in the piston enables a second dose of fluid to be dispensed.

Preferably the apparatus further comprises a second piston in the vessel and which defines a boundary to a third chamber in the vessel for delivery of a third dose of fluid. The apparatus is suitably a handheld device having a manually driven plunger at one end of the vessel whereby pressure is applied by the manual plunger to drive fluid through the vessel. The device may, for example, be a syringe or a manual ratchet driven plunge operated cartridge device such as a mastic gun and cartridge or the like.

Suitably the apparatus is adapted to dispense fluid in a sequence of stages comprising a mixing stage and a dispensing stage. For this the vessel may have a first chamber proximate a dispensing outlet end of the vessel and a second chamber remote from the dispensing outlet end and the piston with bypass passage being between the first chamber and second chamber whereby when the piston moves under pressure from the first position to the second position the bypass passage in the piston opens to allow the fluid in the second chamber to be transferred into the first chamber to mix with the contents of the first chamber, Suitably the fluid held in the second chamber is a liquid and the first chamber holds a solid that dissolves in or otherwise mixes with the liquid.

Preferably in any of the above embodiments the shoulder at the second position is an annular shoulder. The annular shoulder may preferably be formed by an end wall of the vessel or by a piston or by a ring that is connected to the wall of the vessel. For a ring that is connected to the wall of the vessel this is suitably by frangible connections that break when the piston is pressured sufficiently, such as when a manual drive plunger presses directly against the piston and the piston against the ring.

According to a further aspect of the invention there is provided a piston for use in a dosing or dispensing vessel, where the piston moves from a first position in the vessel to a second position for dispensing a dose of fluid from the vessel, the piston having a bypass passage that extends therethrough and which has a valve member that is opened by a valve actuating plunger in the piston that moves within the piston to push the valve open when the valve actuating plunger abuts a shoulder at or near a second position in the vessel.

According to a yet further aspect of the invention there is provided apparatus for dosing a fluid/water-filled system with one or more treatment chemicals/fluid, the apparatus comprising: a vessel; an inlet pipe or hose and an outlet pipe or hose for coupling to the system so that fluid/water may flow into the vessel and fluid from the vessel may flow from within the vessel out of the vessel and into the system, the vessel having a piston therewithin and the vessel wall defining a cylinder in which the piston moves under pressure of incoming fluid from a first position at which the vessel contains fluid to be dispensed to a second position corresponding to substantially complete emptying of the vessel, wherein the apparatus has a bypass passage through or around the piston that opens when the piston substantially reaches the second position so that fluid/water from the system may flow passed the piston when the piston is at the second position. This arrangement allows the apparatus to safely and relatively accurately and rapidly dispense all of the chemical content of the vessel into the system. The opening of the passage prevents back pressure build up when the piston has travelled to its second position and ensures that the vessel may be fully flushed by the normal inflowing system fluid/water subsequently.

Preferably the vessel allows viewing of the movement of the piston. It is preferably a transparent vessel or has a transparent portion of wall to allow the user to view the piston moving into the second position. A pressure gauge may also be provided to monitor the pressure in the vessel and suitably is mounted on the exterior of the vessel and coupled to the interior of the vessel by a conduit. Preferably the pressure gauge is coupled to the interior of the vessel on the side of the piston where fluid flows into the vessel. The gauge provides warning if there is any obstruction and also allows the user to check that the device is operating correctly and with a desired level of pressure of the fluid in the vessel. In general the pressure will correspond to that of the water supply into the vessel but may be adjusted upwardly or downwardly if required, to give a faster or slower rate of flushing for optimal flushing/dosing effectiveness. The pressure or rate of flushing may be adjusted before use by the selection of the tightness of friction fit of the piston. The piston suitably has elastomeric O-rings/sealing rings to seal the circumference of the piston to the wall of the cylinder of the vessel.

Preferably the vessel is formed with a hollow central cylindrical body that is initially open at each end and has a first end plate and a second end plate mounted thereto each to sealingly close off a respective open end, at least one of which is readily demountable following use to allow for ease of maintenance. Suitably the demountable plate is bolted in place to the cylindrical body. In the preferred embodiment the first end plate is bolted to the second end plate, sandwiching and clamping the cylindrical body therebetween.

The dosing device of this aspect provides a new, easier way of adding chemicals into, for example, a sealed central heating system. For the domestic market it is suitably provided with a vessel of capacity corresponding to the commonest commercial size of chemicals pack for treating domestic sealed central heating systems. Currently this is a 1 liter capacity. For the commercial market, ie for larger premises such as schools, hospitals, offices and industrial premises, it is suitably provided with a larger vessel that may be of the order of 5 liters in capacity or larger and suitably corresponds to the larger sizes of chemicals packs available on the market or to multiples of available pack sizes. If a user only needs to add 1 liter of inhibitor fluid there is no need for draining the central heating system.

The dosing device can couple into the filling loop of the central heating system and the pressure of the water in the system pushes the liquid chemicals ahead of it, undiluted, into the central heating system. The user has complete control of the amount of chemical they add to the system.

Once the full content of the vessel has entered the system the device then lets the water flow through the vessel, through or passed the piston and into the system as desired, giving the user full control the whole time unlike the existing prior art devices. With the present device the user can see all of the chemicals going into the system and can control substantially exactly how much is going in. There need be no residual chemical left in the vessel after the initial flush operation, unlike prior art in-line flushing systems such as that disclosed in G82442008A, where the volume of liquid left in the vessel when it is uncoupled may contain some of the chemical.

For other fluidic systems, circulatory or not, as diverse as eg medical drips where the treatment chemical/fluid might be a chemical (drug) for treatment of the patient; or for use in industrial fluid systems such as eg fuel systems or fluid distribution systems or food manufacturing systems, the treatment chemical/fluid might be for lubrication or antifreeze or indeed any other need intrinsic or external to the system.

Each dose, whether for fluidic systems or delivery by syringe or caulking gun or the like may be a predetermined amount/volume of chemical or treatment fluid or medicament and by the invention the dose may be administered easily and reliably with minimal wastage.

BRIEF DESCRIPTION OF THE DRAWINGS

The present invention will now be more particularly described by way of example, with reference to the accompanying drawings, wherein;

FIG. 17 is a side elevation part-sectional view through a yet further variant of the twin dose syringe having a hollow first operating plunger with a valve in the piston part of that hollow plunger, as supplied for use—while the next three figures illustrate the stages of use;

FIG. 18 is a view of the FIG. 17 syringe with the hollow plunger retracted to draw a fluid into the main chamber of the syringe body;

FIG. 19 shows the FIG. 17 syringe with the piston end of a conventional syringe plunger inserted into the first end of the hollow plunger and the hollow plunger being advanced towards the dispensing outlet end of the syringe to push the fluid from within the main chamber of the syringe body; and FIG. 20 shows the FIG. 17 syringe with the hollow plunger seated against the dispensing outlet end of the syringe and thereby opening the valve in the hollow plunger and the conventional syringe plunger being advanced further into the hollow plunger and driven towards the dispensing outlet end of the syringe to push the fluid from within the chamber of the hollow plunger to be dispensed out through the dispensing outlet.

DESCRIPTION OF THE PREFERRED EMBODIMENTS

Figure 1:
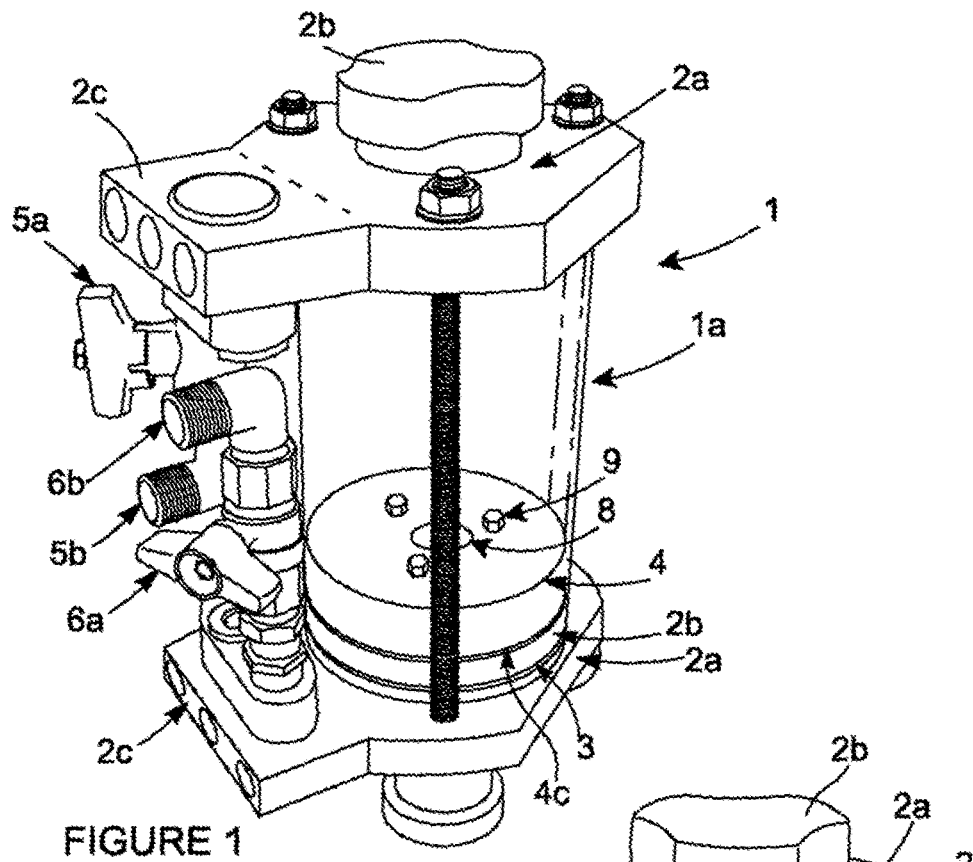
FIG. 1 is a right side perspective view of the vessel of the device for dosing a fluid system.
Figure 2:
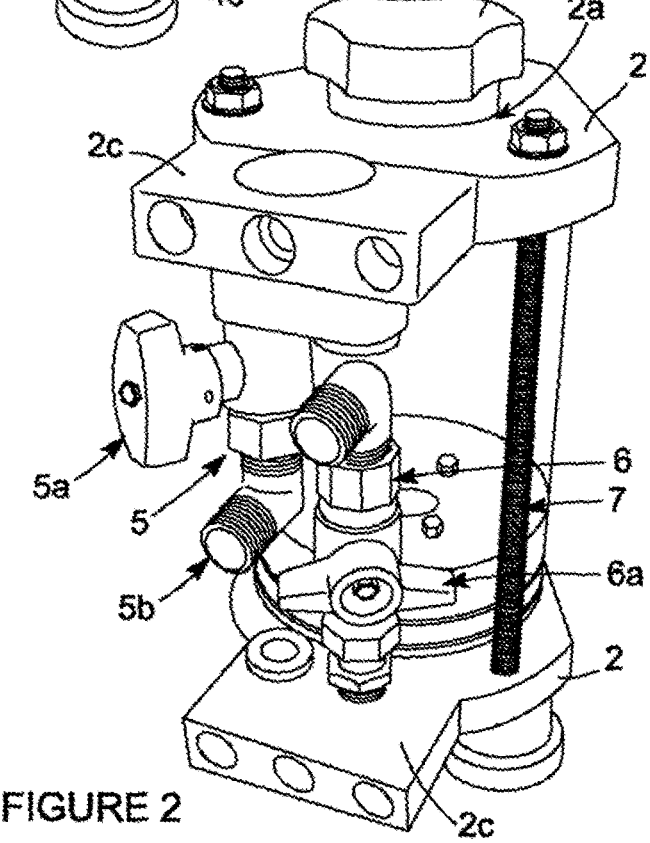
FIG. 2 is a frontal perspective view of the vessel of the device.
Figure 3:
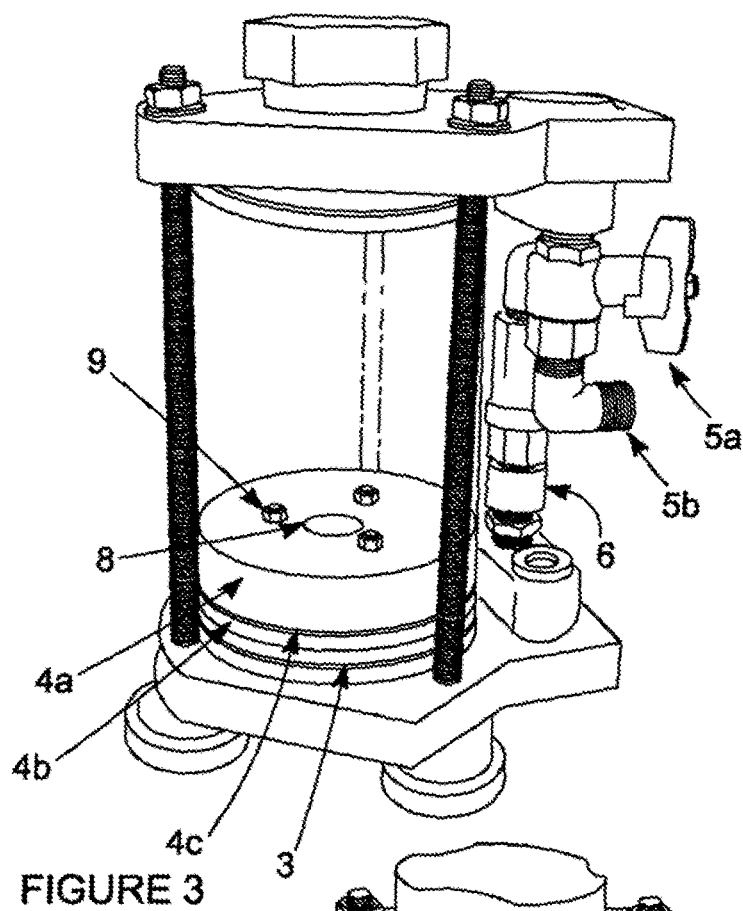
FIG. 3 is a left side perspective view of the vessel of the device.

Referring to FIGS. 1 to 3, the device for treating circulatory fluid systems such as central heating systems with a dose of chemicals comprises a vessel 1, as shown, with a transparent tubular cylindrical body 1a that is blanked off at top and bottom ends by respective end plates 2 that are suitably ABS, acrylic or nylon mouldings. Each end plate 2 is configured to project into the respective vessel end as a plug that is sealed by a respective O ring elastomeric seal 3 to the inner wall of the cylindrical body 1a of the vessel. A short cylindrical/discoidal piston 4, preferably moulded of ABS, acrylic or nylon, is slidingly received within the tubular cylindrical body 1a to be able to move up and down from an initial/first position at the floor of the tubular cylindrical body 1a to a second/terminal position at the upper end thereof and in the process drive any fluid within the vessel up and out from the vessel.

The upper end plate 2 has a central circular fill opening 2a with a large screw-threaded cap 2b that is openable to introduce liquid treatment chemicals straight from a commercially available pack into the vessel 1. In most cases the treatment chemical is an aqueous solution of rust inhibitor or other chemical and does not require preliminary liquidifying, mixing or dilution. A full liter of such fluid may be poured into the vessel, filling the liter-capacity holding chamber above the piston 4.

Other than the fill opening 2a, the upper end of the vessel 1 and the upper end plate 2 have no other inflow openings. An outflow opening and passage is provided in the upper end plate 2 in a shelf 2c that projects radially outwardly and which has a fixed length of pipe 5 extending down to a tap 5a and exit coupling 5b at the free lower end of the pipe 5. The upper plate 2 of the vessel projects radially outwardly and holds the pipe 5 away from the body 1a of the vessel.

The device also comprises a pair of coupling hoses (not shown) to couple the vessel into a central heating system, suitably between the cold water supply pipe of the central heating system and the return pipe of the central heating system such as is done in the prior art and illustrated inter alia in GB 2442008A. Exit coupling 5b at the free lower end of the outflow pipe 5 comprises a screw thread on the outside diameter of the pipe 5 to which an end of one of the pair of hoses may be attached.

The base plate 1b of the vessel 1 also has a shelf 2c that projects radially outwardly and this incorporates a short length of feed pipe 6 that runs from an inflow opening into the lower interior of the vessel 1a below the piston 4 to a tap/hand operated valve 6a and inlet coupling 6b. Inlet coupling 61) at the free lower end of the inflow pipe 6 comprises a screw thread on the outside diameter of the pipe 6 to which an end of one of the pair of hoses may be attached and where the other end of the hose is attached to the water supply pipe for the central heating system.

Each end plate 2 is readily demountable from the tubular cylindrical body 1a following use to allow for ease of maintenance. The upper end plate 2 is bolted to the lower end plate 2 by bolts 7 that extend up the full height of the body 1a and the cylindrical body 1a is thus sandwiched and clamped between the respective end plates 2. The unit as a whole is, in the illustrated form, adapted to stand upright on bun-shaped feet at the bottom of the lower plate 2. However, the device may be used in a range of orientations in principle, even inverted, and not simply oriented upright with the water in-feed at the bottom and outflow at the top, Nevertheless the illustrated arrangement suits introduction of the chemical by pouring in from above and is, therefore, the preferred configuration.

Figure 4:
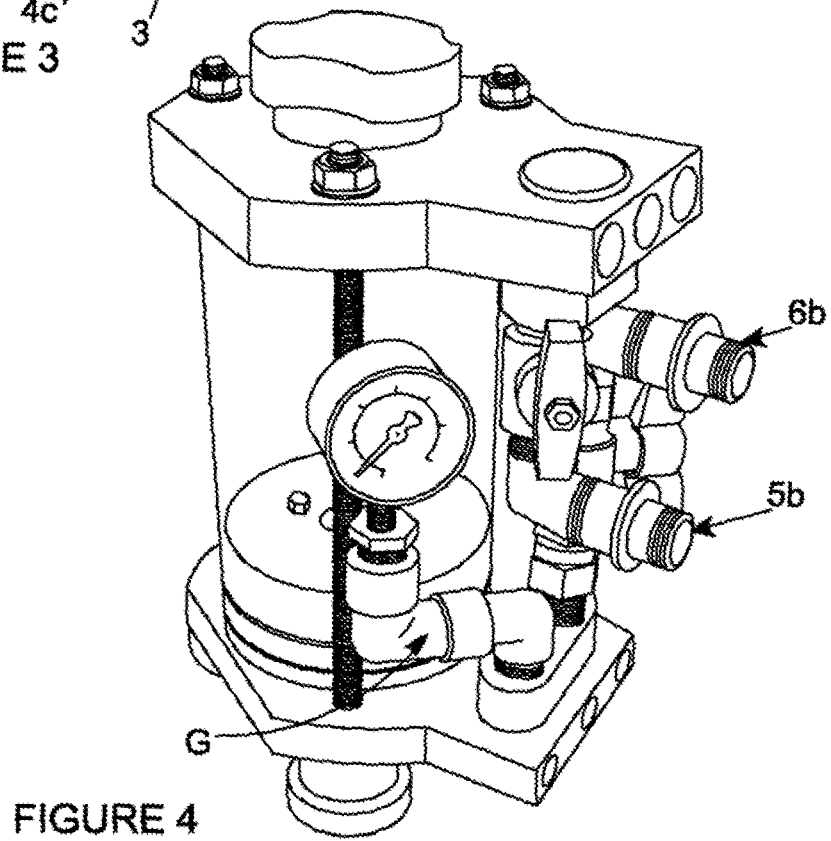
FIG. 4 is a left side perspective view of the vessel of the device similar to FIG. 3 but showing a pressure gauge installed thereon.

As shown in FIG. 4, a pressure gauge G may be coupled to a valved conduit outlet to communicate with the interior of vessel 1a and provide reading of the fluid pressure within the vessel 1a, suitably being the pressure at the water supply/inflow side of the piston 4.

Figure 5:
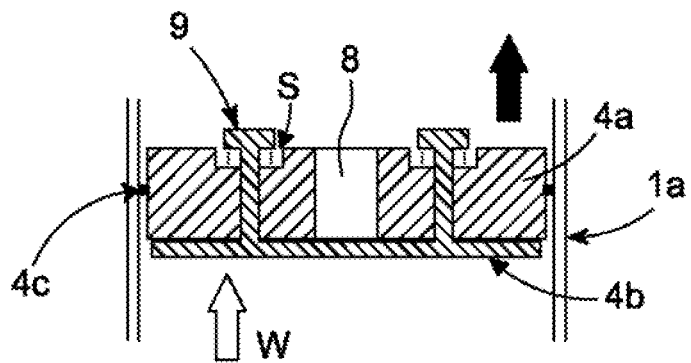
FIG. 5 is a schematic sectional view of the vessel of the device showing the two stage structure of the piston, with the piston in its initial position.
Figure 6:
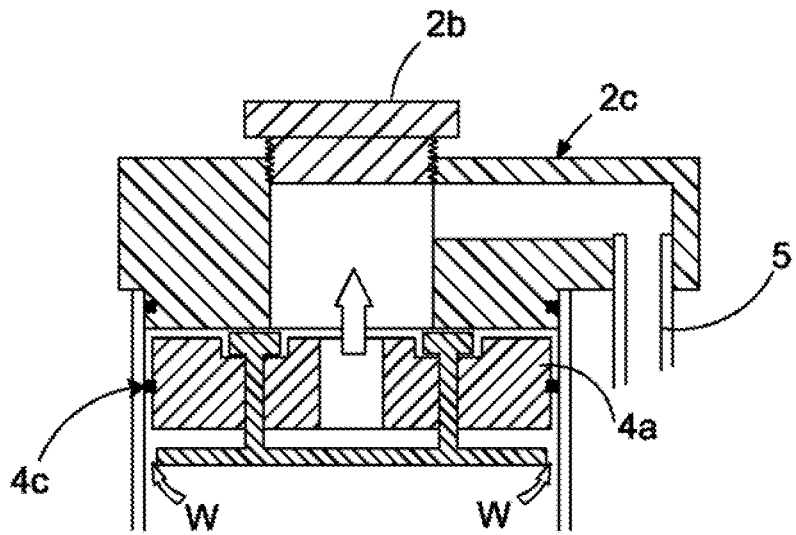
FIG. 6 is a schematic sectional view corresponding to FIG. 5 but showing the piston moved to its second/terminal position and the two stages of the piston shifted a small spacing apart to open up a flow passage through the piston.

Referring now to FIGS. 5 and 6, the piston 4 has an upper stage 4a and a lower stage 4b. The upper stage 4a is of short cylindrical/discoidal form and the lower stage 4b has a thinner discoidal form. An elastomeric O-ring 4c is provided in an annular groove around the outside circumferential surface of the piston upper stage 4a to provide a seal against the bore of the vessel cylindrical body 1a. The upper stage 4a has a broad circular central passage 8 extending up through it to allow water W that has entered the vessel 1 from the central heating system water supply to be expelled through the body of the piston 4 but only when the piston 4 has substantially reached the second position adjacent the upper end of the vessel 1.

Figure 7:
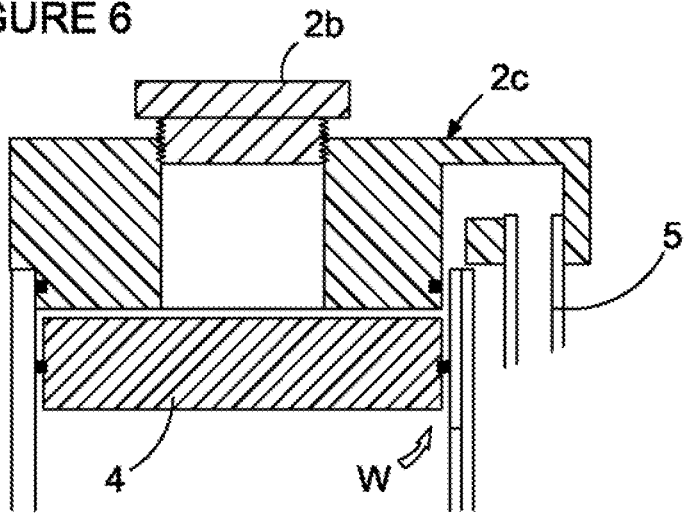
FIG. 7 is a schematic sectional view similar to FIG. 5 but showing a variant/second embodiment in which the bypass passage to bypass the piston is provided as grooves in the cylinder wall of the vessel.

The lower stage 4b of the piston 4 effectively functions as a valve that is moved away from the upper stage 4a by spigots/plungers/actuating mandrels 9 on the lower stage 4b landing on shoulders or the underside of the upper end of the vessel/upper plate 2 while the upper stage 4a continues to move upwardly a small distance. This opens up access to the central passage 8 in the upper stage 4a of the piston 4. The lower stage/valve 4b is spring-loaded by a respective spring S on each spigot/plunger 9 so as to be normally biased to the valve-closed state As an alternative to this spring-loaded valve arrangement one or more internal longitudinal grooves might be machined or otherwise formed in the vessel's tubular cylindrical body 1a at the outlet end, as per the second variant/embodiment shown in FIG. 7, so that as the piston 4 moves against the upper plate 2 the grooves allow the mains water to pass across the piston 4 circumferential surface and flow over the O-ring seal 4c. When such a configuration is used a drain valve would generally be necessary in the inlet end plate/end cap 2 so that the piston 4 may be returned for refilling of the apparatus.

Operating Sequence:

The filler cap 2b is removed and a rod is inserted through the filler cap 2b hole 2a to press against the centre of the piston 4. This pushes against and opens the spring loaded valve 4b allowing the piston 4 to be pushed down against the bottom plate/end cap 2. Any water in the apparatus is now poured out. The desired chemical additive is poured through the filler hole 2a. The filler cap 2b is screwed back in place and the outlet tap/valve 5a is closed. The inlet tap/valve 5b is then closed too and a mains water connected hose is connected to the inlet coupling 6b and heating system connected hose is connected to the outlet coupling 5b. The inlet tap/valve 6a is then opened allowing mains water into the cylinder 1a.

As the pressurised mains water flows into the vessel 1, the piston 4 is pushed towards the upper plate 2 forcing the chemical additive into the heating system. At this stage the chemical additive is separated from the mains water by the piston 4. As the piston 4 reaches the outlet end cap/upper plate 2 the three spigots 9 on the piston valve 4b contact the outlet end cap/upper plate 2 and open the valve 4b allowing mains water to flush the residue of chemical additive into the heating system. The inlet tap/valve 6a can now be used to reinstate the correct pressure in the system. The inlet and outlet valves 5a, 6a are then closed and the apparatus decoupled and removed from the system. The piston 4 is returned to its position against the inlet end cap/bottom plate 2 and the water in the cylinder 1a is emptied. As can thus be appreciated, this whole process is very quick as compared to the prior art and considerably more easy to control and accurate, improving dose usage and operator time and costs.

Turning now to FIGS. 8 to 13, these illustrate an example of the hand-held piston-operated fluid dose dispensing device aspect of the invention. The drawings show a hypodermic syringe but the device may be any syringe (with or without a needle) or any other hand held device that comprises a vessel with sequential chambers divided by a piston and that has a manually powered plunger P to pressurise the fluid in the vessel to be dispensed through a dispensing aperture of the vessel. The drawings could, for example, with minor adjustment, illustrate a ratchet-driven plunger dispensing gun and cartridge with piston such as a mastic gun and cartridge, where the user repeatedly clicks a trigger to advance the plunger against a rear wall of the cartridge to pressurise the fluid flow from the cartridge.

Figure 8:
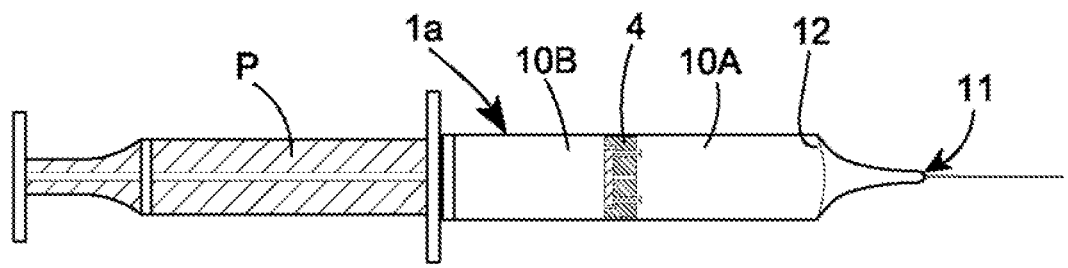
FIG. 8 is a side elevation part-sectional view through a device embodying a hand-held piston-operated device aspect of the invention and comprising a syringe (e.g. hypodermic syringe) suitable for dispensing two doses of the same or different medicaments sequentially.
Figure 9:
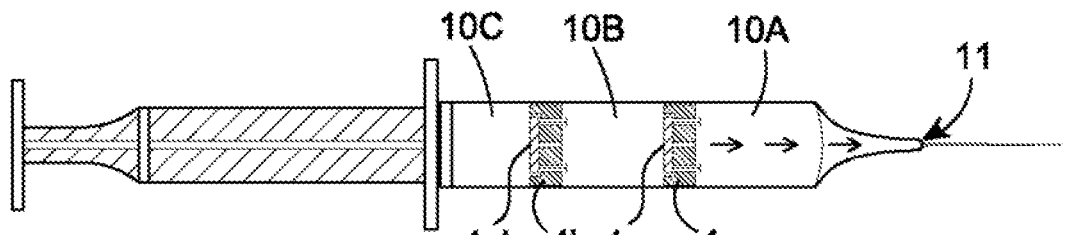
FIG. 9 is a side elevation part-sectional view through a variant of the hand-held piston-operated device that differs in being suitable for dispensing three doses of the same or different medicaments sequentially by having a second piston dividing the vessel into a third sequential chamber.
Figure 10:
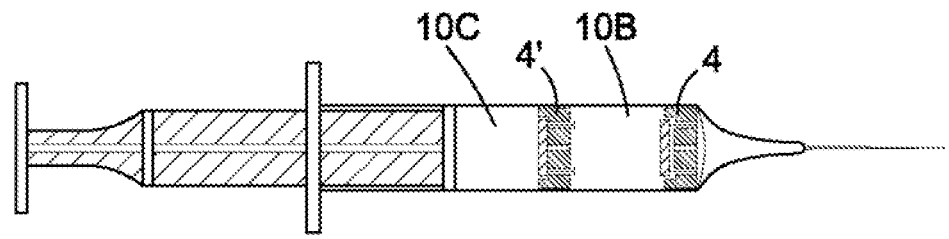
FIG. 10 is a view corresponding to FIG. 9 but in which the plunger of the syringe has been depressed and the first piston, separating the first and second chambers and thereby defining the first dose volume, has reached its second/terminal position abutting the shoulder of the syringe at the dispensing aperture and is substantially emptied and the valve in that piston is opened to deliver the dose from the second chamber through the first piston.
Figure 11:
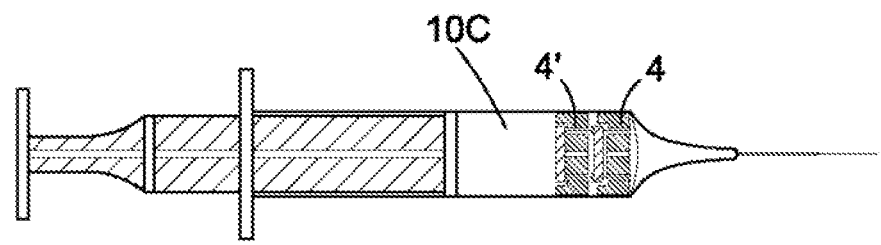
FIG. 11 is a view corresponding to FIG. 10 but in which the plunger is further depressed to the point where the second piston, separating the second and third chambers and thereby defining the second dose volume, has reached its second/terminal position abutting the first piston at the dispensing aperture and is substantially emptied and the valve in that second piston is opened to deliver the dose from the third chamber through the second piston and thence through the open first piston.
Figure 12:
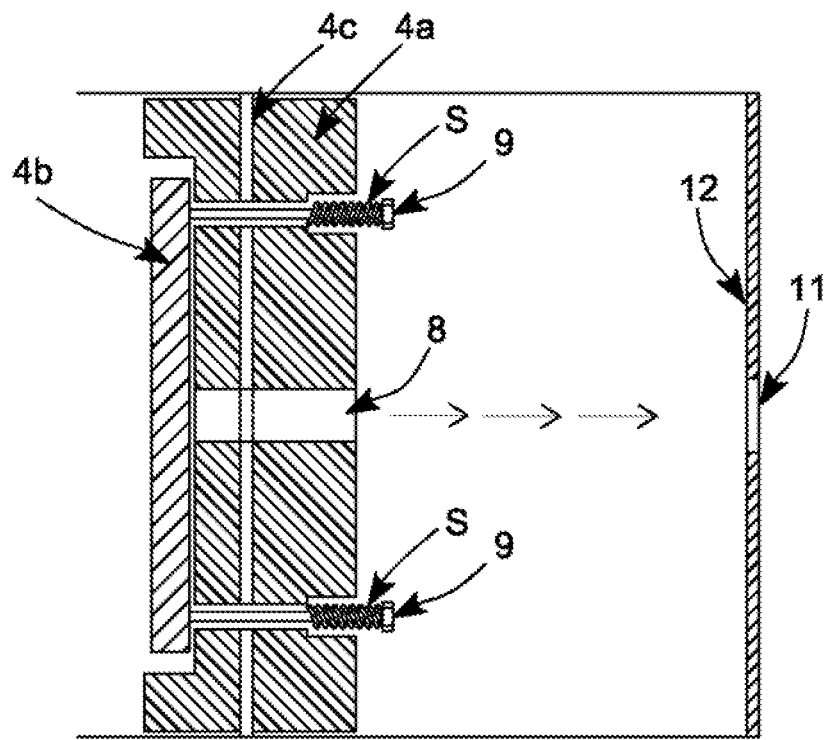
FIG. 12 is a close-up view of the first piston in FIG. 8 or 9 approaching the dispensing aperture and dispensing the dose from the first chamber.
Figure 13:
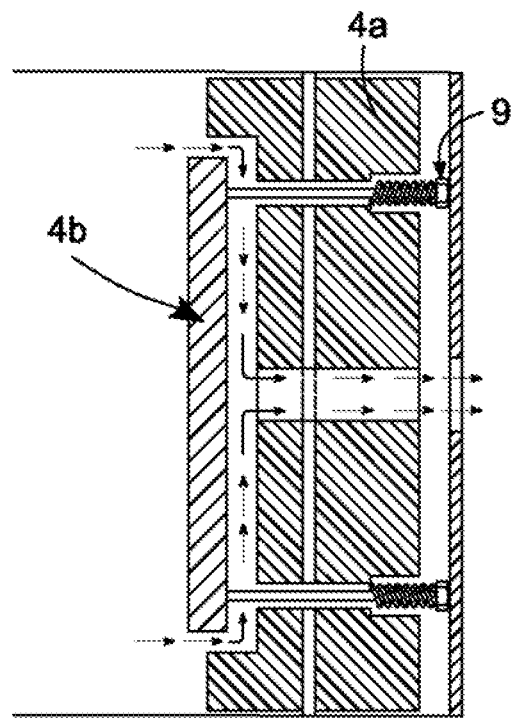
FIG. 13 is a close-up view of the first piston in FIG. 10 at the point where the first piston has reached its second/terminal position abutting the shoulder of the syringe at the dispensing aperture and is substantially emptied and the valve in that first piston is opened to deliver the dose from the second chamber of the syringe vessel through the first piston.

The hand-held piston-operated fluid dose dispensing device of FIG. 8 has two chambers, a first chamber 10A closest to the dispensing aperture 11, and a second chamber 10B separated from the first chamber 10A by a piston 4. This device is suitable for dispensing two doses of the same or different medicaments (or other fluids/chemicals) sequentially. In common with the piston-operated fluid dose dispensing device of FIGS. 1 to 6, the device of FIG. 8 has a cylindrical vessel 1a with a piston 4 having an O-ring around its circumference to seal against the inner surface of the cylindrical sidewall of the vessel 1a and the piston 4 is modified to have a bypass passage 8 therethrough and which is closed off in normal operation of the piston 4 by a spring-loaded piston valve 4.

The spring-loaded piston valve 4b is opened by a pair of spigots 9 (which also may be referred to as valve actuating plungers/actuating mandrels 9) on the piston 4, when the piston 4 lands on the shoulders 12 at the dispensing aperture 11 end of the vessel 1a while the upper piston 4 continues to move towards that end a small distance. This opens up access to the central passage 8 (see FIG. 14), allowing fluid from the second chamber 10B to now flow through the piston 4 to the dispensing aperture 11 of the vessel 1a. The valve 4b is spring-loaded by a respective spring S on each spigot/valve actuating plunger 9 so as to be normally biased to the valve-closed state. In operation the hand-held piston-operated fluid dose dispensing device of FIG. 8 can be used to deliver sequentially two doses of the same medication or two doses of different medication and avoids need for multiple syringes or bulky manifold style multiple tube parallel syringes. The piston 4 with integral bypass passage and valve 4a can be retro-fitted to existing syringe vessels if desired and the arrangement is very versatile. Indeed, referring to FIGS. 9 to 11 the syringe can be made to deliver sequentially three doses of the same medication or three doses of different medication simply by installing a second piston 4' with integral bypass passage and valve 4a' into the vessel 1a. Here the second piston 4' may differ from the first piston 4 only in that the valve 4a is of smaller diameter and the valve actuating plungers 9 are less far apart so that the valve 4a' of the second piston 4' can use the rear surface of the first piston 4 as the shoulder on which the valve actuating plungers 9 of the second piston 4' land to open the valve 4a' (see FIG. 11). Thereby the syringe can dispense the doses from the first and second chambers 10A and 10B sequentially in the same manner as in the two chamber embodiment and can then dispense the dose from the third chamber 10C as the second piston 4' presses up against the first piston 4 and the plunger P then pushes the fluid in the third chamber 10C out through the bypass passage 8 of the second piston 4 and thence out through the first piston 4 and out the dispensing aperture 11.

Figure 14:
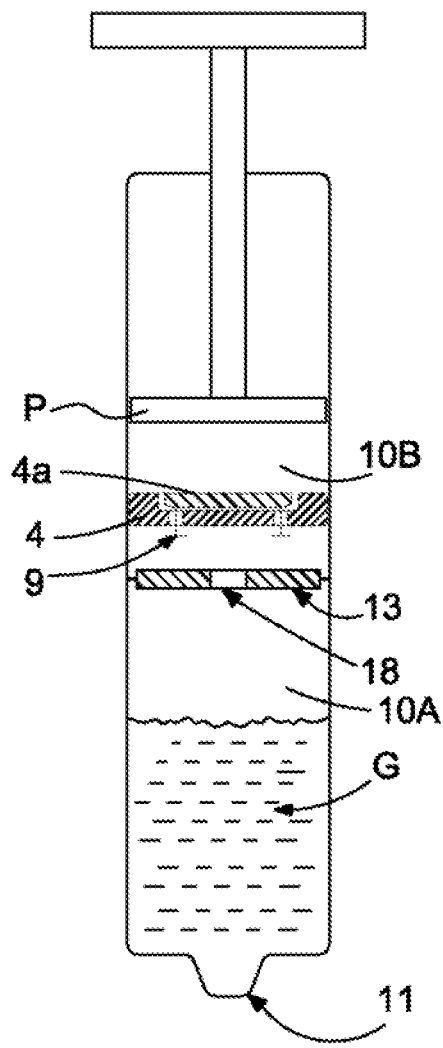
FIG. 14 is a side elevation part-sectional view through a further variant of the hand-held piston-operated device similar to the FIG. 8 embodiment but that primarily differs in being suitable for dispensing doses in sequential stages beginning with transferring the dose from the second chamber remote from the vessel's dispensing aperture into the first chamber by having the annular shoulder to open the piston's valve provided not on the vessel end wall but rather as a ring that is connected to the vessel sidewall at a selected point partway along the vessel.
Figure 15:
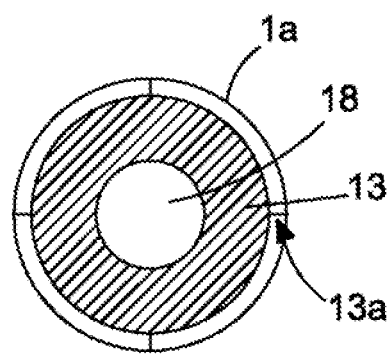
FIG. 15 is an end elevation view of the ring in situ.
Figure 16:
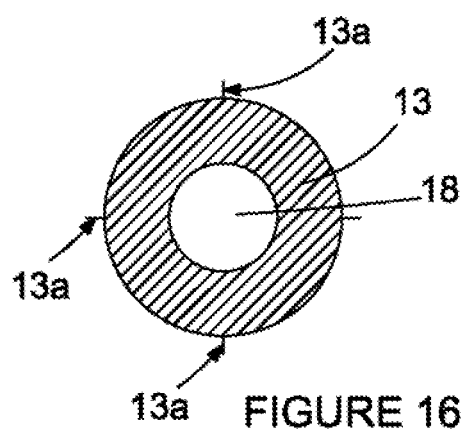
FIG. 16 is an end elevation view of the ring and frangible connecting elements shown separated from the vessel.

Referring now to FIGS. 14 to 16, these show a further variant of the hand-held piston-operated fluid dose dispensing device and which is suitable for dispensing doses in sequential stages. It will be noted that in this variant the annular shoulder to open the piston's valve 4a is provided not on the vessel end wall 12 but rather as a ring 13 that is connected to the vessel sidewall at a selected point partway along the vessel 1a by frangible connection arms 13a. The dispensing stages begin with transferring the dose from the second chamber 10B remote from the vessel's dispensing aperture 11 into the first chamber 10A by depressing the manually driven plunger P. This moves the piston 4 down the vessel 1a until the valve actuating plungers 9 of the piston 4 land on the shoulder formed by the ring 13. There the valve actuating plungers 9 are pushed up to unseat the valve 4a and open the passage 8 through piston 4 so that liquid from the second chamber 10B is forced through the passage 8 of the piston 4, then through the central aperture 18 of the ring 13 and into the first chamber 10A. The frangible connection arms 13a hold the ring 13 in place initially until greater force is applied to the plunger P. In the interim the user can shake the vessel 1a to mix the fluid from the second chamber 10B with the content of the first chamber 10A before the user then pushes down harder on the plunger P to break the frangible connection arms 13a allowing the ring 13 to advance with the plunger P for the now mixed contents of the first chamber 10A to be dispensed.

The vessel 1a may be a syringe, with or without a needle, but need not be. As illustrated the device is a syringe but is not a hypodermic syringe and the dispensing outlet 11 is capped off by an adhered foil tab or other cap that is suitably secure enough to prevent any dosing fluids escaping in the initial mixing stage (though it may allow venting to reduce pressure when the piston advances for the mixing step). In the example illustrated in FIG. 14 the first chamber 10A contains a solid G in powder or granular form with a head of air above, while the second chamber 10B contains a liquid to be mixed with the solid when the piston 4 is pressed the small distance down to the level of the ring 13. The device's arrangement can be used for a wide variety of purposes with different combinations of types and states of materials and is particularly useful where the material involved has greater longevity, is stabilised or is inactive prior to mixing. For example the second chamber 106 may contain water while the first chamber 10A contains an aqueous soluble powder that is inactive or has a longer shelf life in the dry state before it is dissolved in the water.

In a further variant of the syringe embodiments, as illustrated in FIGS. 17 to 20, the syringe has not one but two main plungers P, P1 to operate it to drive the fluid contents of the syringe out through the dispensing outlet of the syringe. One plunger P is of conventional/standard type with the normal rigid/solid stem with a handle H at the first end and a part at the other end that is a piston PP to push the fluid ahead of it. The other of the main plungers P1 of the syringe of FIGS. 17 to 20 is unconventional. It has a substantially circular cylindrical hollow body into which the conventional syringe plunger P may be driven. In this embodiment the interior of the cylindrical hollow body of plunger P1 serves as a chamber C1 that holds one dose of a fluid to be dispensed while the syringe vessel 1a internal chamber C2 holds another. The dose of fluid in the chamber C1 of the syringe plunger may be pre-filled into the chamber C1 and held there by a frangible membrane/sealing cover that is penetrated or removed when the standard plunger P is inserted into the hollow plunger P1. The hollow plunger P1 has a piston part 40 that equates to the piston part PP of the standard plunger P. However, the piston part 40 of plunger P1 is not a standard piston part, it has a bypass valve. Piston part 40 is the same as the bypass valve-incorporating-piston 4 in the preceding embodiments, suitably having all of the same features as the piston 4 in the preceding embodiments. In other words the piston part 40 of the plunger P1 incorporates the bypass passage 8 therethrough and which is sealed by the closure 4b and that opens when the valve actuating plungers 9 of the piston 4 land on the end face 12 of the syringe.

As shown in FIG. 17 the syringe has the chamber C1 of the hollow plunger P1 filled with a first medicament dose and the hollow piston P1 is housed in the interior of the syringe vessel 1a but the valve actuating plungers 9 of the bypass valve of the piston part 40 are not quite contacting the endwall/shoulder at the dispensing end of the syringe. The handle 111 of the hollow plunger P1 is braced in this position by frangible (breakable) struts or clips 41 that project from the inner face of the handle H1. The struts or clips 41 are broken/removed when readying the syringe for use and the syringe's chamber C2 is filled with a further dose of the same or a different fluid/medicament as illustrated in FIG. 18. Then, to dispense/administer the doses, first the standard plunger P is inserted into the mouth of the chamber C1 of the hollow plunger P1 and the hollow plunger P1 is then gradually advanced to administer the dose from the syringe chamber C2 until the piston part 40 of the hollow plunger P1 reaches the endwall at the dispensing outlet end of the syringe whereupon the bypass valve 4b of the piston part 40 is opened. Then the standard plunger P is gradually advanced into the chamber C1 of the hollow piston P1 to administer the dose from the piston P1.

I claim:

1. Apparatus for dispensing a dose of fluid, the apparatus comprising a dispensing vessel with a dispensing outlet, the vessel having a piston and a vessel wall defining a cylinder in which the piston may move under pressure from a first position to a second position, wherein the apparatus has a bypass passage that extends through the piston and has a valve member that is opened by a valve actuating plunger in the piston that moves within the piston to push the valve open when the valve actuating plunger abuts a shoulder at or near the second position in the vessel; wherein the shoulder at the second position is an annular shoulder, and wherein the apparatus is adapted to dispense fluid in a sequence of stages comprising a mixing stag and a dispensing stage.

2. Apparatus as claimed in claim 1, wherein the apparatus is adapted to dispense two dr more doses of fluid in sequence and the vessel has at least a first chamber and a second chamber separated by the piston.

3. Apparatus as claimed in claim 1, wherein the apparatus is a handheld device having a manually driven plunger at one end of the vessel whereby pressure is applied by the manual plunger to drive fluid through the vessel from said one end to a dispensing outlet at the other end of the vessel.

4. Apparatus as claimed in claim 3, wherein the apparatus is a syringe.

5. Apparatus as claimed in claim 1, wherein the annular shoulder is formed by a ring that is connected to the wall of the vessel.

6. Apparatus as claimed in claim 5, wherein the ring is connected to the wall of the vessel by frangible connections that break when the piston is pressured.

7. Apparatus as claimed in claim 6, wherein the frangible connections are configured to break when a manual plunger presses directly against the piston and the piston against the ring.

8. Apparatus for dispensing a dose of fluid, the apparatus comprising a dispensing vessel with a dispensing outlet, the vessel having a piston and a vessel wall defining a cylinder in which the piston may move under pressure from a first position to a second position, wherein the apparatus has a bypass passage, that extends through the piston and has a valve member that is opened by a valve actuating plunger in the piston that moves within the piston to push the valve open when the valve actuating plunger abuts a shoulder at or near the second position in the vessel wherein the shoulder at the second position is an annular shoulder, wherein the vessel has a first chamber proximate a dispensing outlet end of the vessel and a second chamber remote from the dispensing outlet end and a piston between the first chamber and second chamber whereby when the piston moves under pressure from the first position to the second position the bypass passage in the piston opens to allow the fluid in the second chamber to be transferred into the first chamber to mix with the contents of the first chamber.

9. Apparatus as claimed in claim 8, wherein the fluid held in the second chamber is a liquid and the first chamber holds a solid that dissolves in or otherwise mixes with the liquid or is, also a liquid.

* * * * *